(12) United States Patent
Marsh

(10) Patent No.: US 11,426,550 B2
(45) Date of Patent: Aug. 30, 2022

(54) MICRO BI-DIRECTIONAL VALVES AND SYSTEMS

(71) Applicant: Encite LLC, Burlington, MA (US)

(72) Inventor: Stephen Alan Marsh, Carlisle, MA (US)

(73) Assignee: Encite LLC, Burlington, MA (US)

( * ) Notice: Subject to any disclaimer, the term of this patent is extended or adjusted under 35 U.S.C. 154(b) by 879 days.

(21) Appl. No.: 16/242,083

(22) Filed: Jan. 8, 2019

(65) Prior Publication Data
US 2019/0209797 A1   Jul. 11, 2019

Related U.S. Application Data

(60) Provisional application No. 62/615,064, filed on Jan. 9, 2018.

(51) Int. Cl.
*A61M 16/06* (2006.01)
*F16K 99/00* (2006.01)
(Continued)

(52) U.S. Cl.
CPC ........ *A61M 16/06* (2013.01); *A61M 16/0057* (2013.01); *A61M 16/0666* (2013.01);
(Continued)

(58) Field of Classification Search
CPC ........ A61M 16/20–201; A61M 16/208; A61M 39/223; A61M 39/24; A61M 2039/224; A61M 2039/2406–242; A61M 2039/2473; A61M 2039/2493; F16K 99/0011–0013; F16K 99/0028; F16K 99/0055–0057; F16K 99/0086; F16K 11/00–02;
(Continued)

(56) References Cited

U.S. PATENT DOCUMENTS 6,443,154 B1   3/2002   Jalde et al.
6,372,112 B1   4/2002   Bibi
(Continued)

OTHER PUBLICATIONS

European Search Report, PCT/US1029/012828, dated Sep. 7, 2021, p. 1-10.
(Continued)

*Primary Examiner* — Rachel T Sippel
(74) *Attorney, Agent, or Firm* — Fish & Richardson P.C.

(57) ABSTRACT

Disclosed is a bi-directional exhalation valve useful for many applications such as in CPAP devices. The exhalation valve includes a valve body having a center chamber, side chambers, and bidirectional ports coupled to the center chamber via passages and a mechanism that provides fluid ingress into the bi-directional valve in a first mode of operation or fluid egress from the bi-directional valve in a second mode of operation. Unidirectional ports are coupled to the plurality of bidirectional ports to provide providing fluid egress from the valve in the second mode of operation, and a unidirectional port provides fluid ingress into the bi-directional valve in the first mode of operation. A mechanism including a center paddle, side paddles, and a shaft are arranged in an elongated compartment of the valve body, such that the shaft is pivots and the central and side paddles open and close corresponding ones of the input and output ports.

16 Claims, 7 Drawing Sheets

(51) Int. Cl.
*F04B 19/00* (2006.01)
*A61M 16/00* (2006.01)
*A61M 16/20* (2006.01)
*F04B 23/04* (2006.01)

(52) U.S. Cl.
CPC ........ *A61M 16/201* (2014.02); *A61M 16/208* (2013.01); *F04B 19/006* (2013.01); *F04B 23/04* (2013.01); *F16K 99/0011* (2013.01); *F16K 99/0028* (2013.01); *F16K 99/0055* (2013.01); *A61M 16/0683* (2013.01); *F16K 2099/0086* (2013.01); *F16K 2099/0094* (2013.01)

(58) Field of Classification Search
CPC ......... F16K 11/04; F16K 11/052–0525; F16K 11/072–074; F16K 11/0746; F16K 15/00–02; F16K 15/026; F16K 15/03; F16K 15/035; F16K 17/02; F16K 17/18; F16K 27/02–0232; F16K 27/0623; A62B 9/02; A62B 18/10
See application file for complete search history.

(56) References Cited

U.S. PATENT DOCUMENTS

| | | | |
|---|---|---|---|
| 9,352,115 | B1 | 5/2016 | DeStefano |
| 2005/0172967 | A1 | 11/2005 | McAuliffe et al. |
| 2008/0142013 | A1 | 6/2008 | Hallett et al. |
| 2012/0304988 | A1 | 6/2012 | Meyer et al. |
| 2015/0034192 | A1* | 2/2015 | Hossfeld ................ F01N 5/02 137/625.44 |
| 2015/0136137 | A1* | 5/2015 | Bugamelli ........ A61M 16/0683 128/205.24 |
| 2016/0131126 | A1 | 5/2016 | Marsh |

OTHER PUBLICATIONS

International Search Report and Written Opinion, PCT/US19/12828, dated Mar. 22, 2019, pp. 1-14.

* cited by examiner

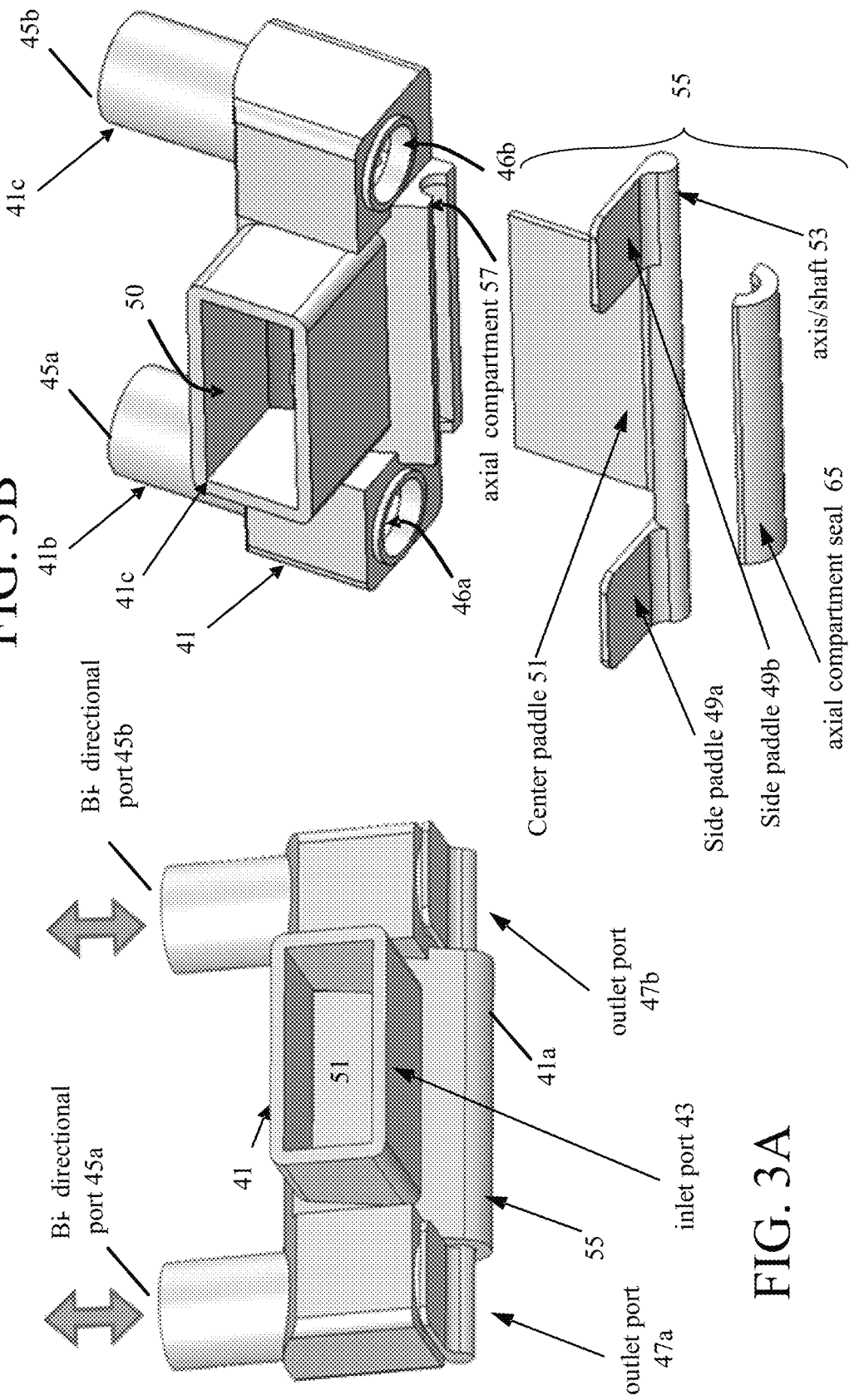

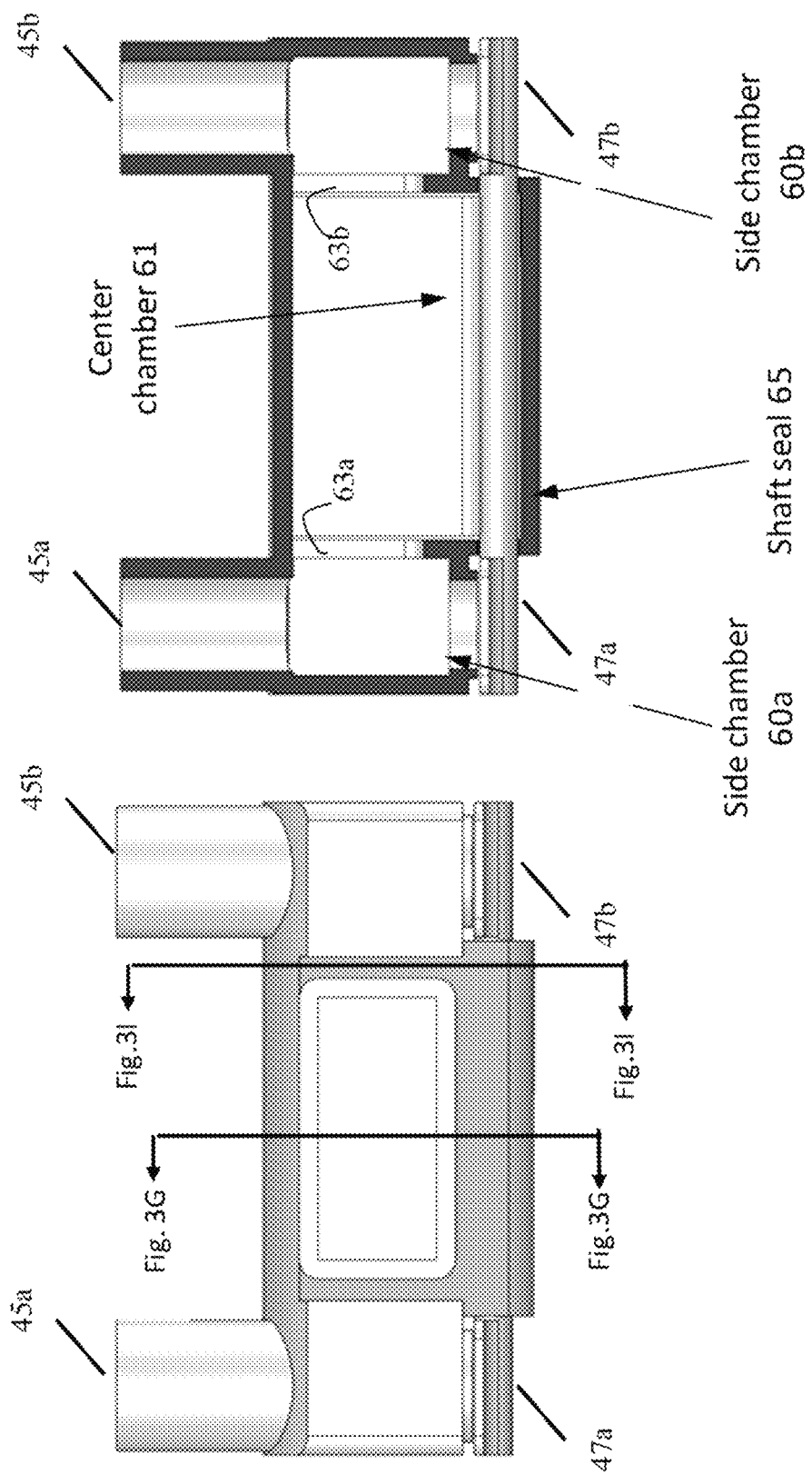

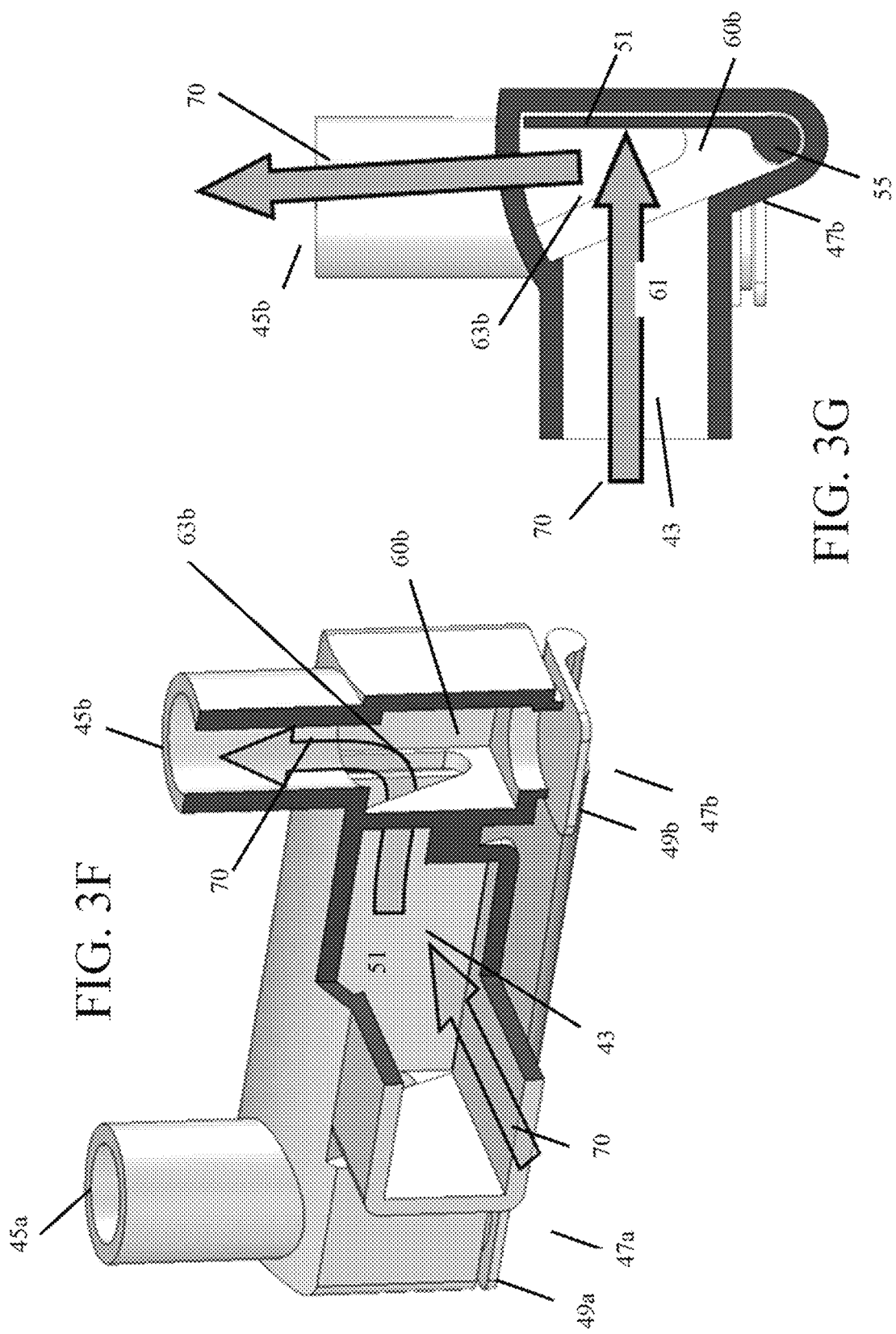

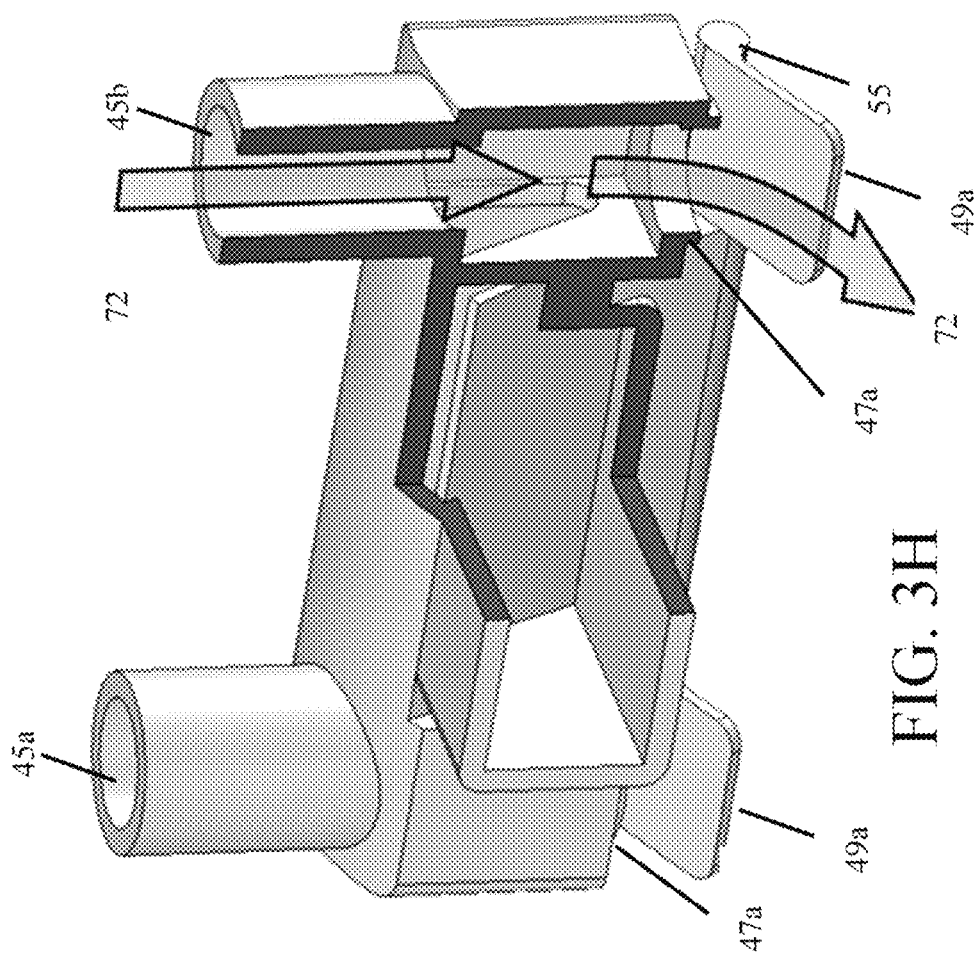
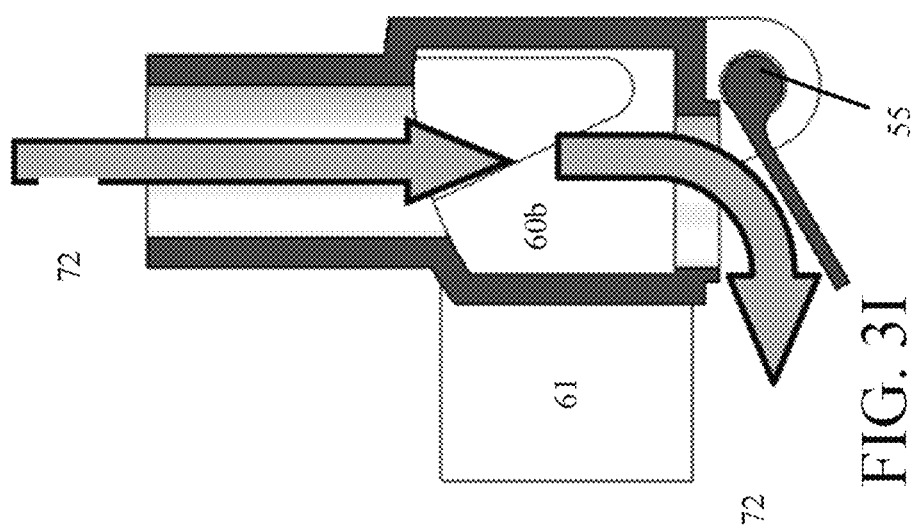
FIG. 3H
FIG. 3I

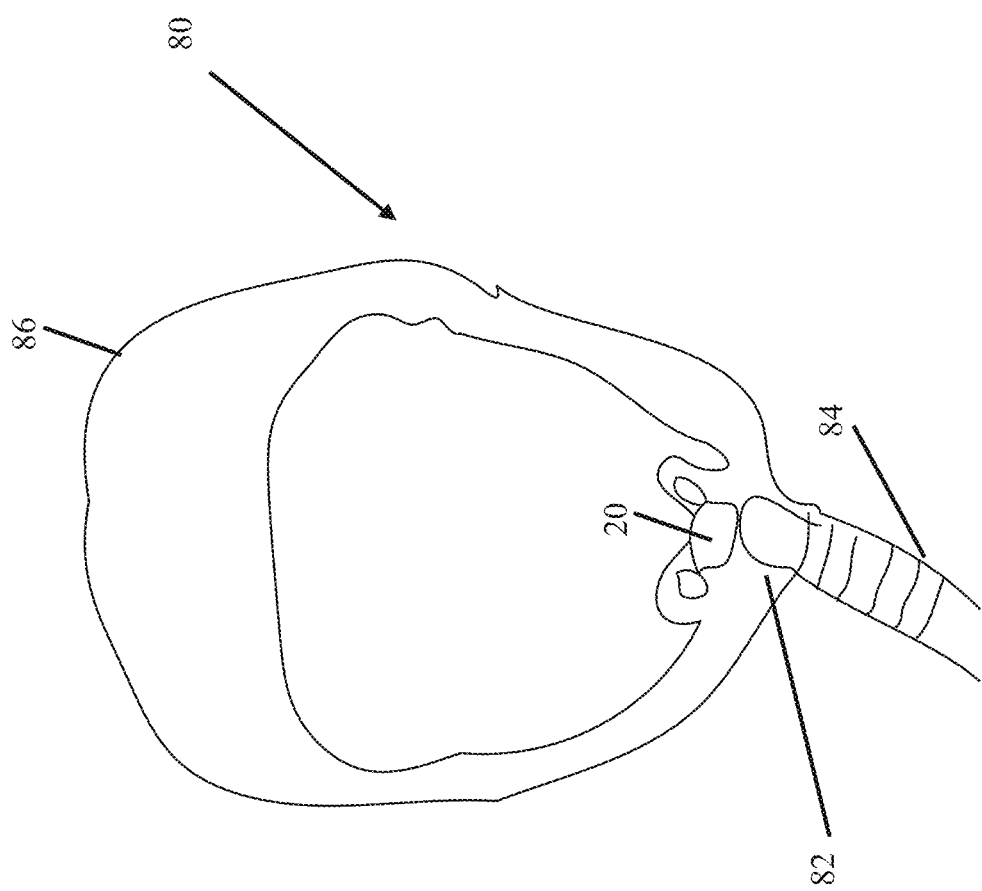

MICRO BI-DIRECTIONAL VALVES AND SYSTEMS

PRIORITY CLAIM UNDER 35 U.S.C. § 119

This application claims priority under 35 U.S.C. § 119 to U.S. Provisional Patent Application Ser. No. 62/615,064, filed Jan. 9, 2018, and entitled "Micro bi-Directional Valves and Systems," the entire contents of which are hereby incorporated by reference.

BACKGROUND

This specification relates to fluid flow systems and in particular CPAP devices.

A somewhat common medical disorder, sleep apnea, involves a reduction or pause in breathing (airflow) during sleep. Sleep apnea is common among adults but rare among children. Treatments for sleep apnea can include surgical procedures or nonsurgical treatments that can involve behavioral changes dental appliances and mouthpieces. One nonsurgical treatment involves CPAP (continuous positive airway pressure) devices.

Continuous positive airway pressure (CPAP) is a non-surgical treatment that uses a machine to supply air pressure to hold a user's airway open so that it does not collapse during sleep. A machine delivers air through a nasal or face-mask under pressure. The machine blows heated, humidified air through a tube to a mask that is worn snugly to prevent the leakage of air. Masks come in several forms including nasal pillows, nasal masks, and full-face masks. Various CPAP machines are in use. Typically, the CPAP machine is a little larger than a toaster, it is generally portable so that it can be taken on trips. However, existing CPAP treatments are not easy to use, as it is not easy to sleep with a mask that blows air into the nose also such CPAP machines/masks are generally required to be cleaned periodically so as to avoid build-up of bacterial, viruses, etc.

One example of a miniature CPAP device that is based on a micro pump (or micro blower) is disclosed in US-2015-0267695-A1 and another is disclosed in US-2016-0131126-A1, the entire contents of which are incorporated herein by reference.

SUMMARY

Disclosed here in a bi-directional valve. By bi-directional is meant that airflow into and out of the valve occurs on a bidirectional port side with relative ease such that outflow of air does not encounter significant resistance from a continuous inflow of air in the bi-directional valve.

While such a valve would be useful in many applications, it is especially useful in a miniature CPAP device as disclosed in US-2015-0267695-A1 and US-2016-0131126-A1. Such CPAP devices are configured to be very small, in comparison to the more conventional CPAP devices. Such a valve could also be useful with the more conventional CPAP devices and especially in masks used with these more conventional CPAP devices.

According to an aspect, a valve includes a valve body having a center chamber, a plurality of side chambers, and an elongated compartment and a plurality of bidirectional ports coupled to the center chamber via a set of passages to provide fluid ingress into the bi-directional valve in a first mode of operation or fluid egress from the bi-directional valve in a second mode of operation, and a plurality of unidirectional ports coupled to the plurality of bidirectional ports to provide providing fluid egress from the valve in the second mode of operation, and a single unidirectional port to provide fluid ingress into the bi-directional valve in the first mode of operation, a mechanism including a center paddle and a plurality of side paddles, and a shaft supporting the center paddle and the plurality of side paddles along the length of the shaft, the shaft disposed in the elongated compartment of the valve body and allowed to pivot to cause the center paddle and the plurality of side paddles to open and close the input and output ports according the first and second modes.

According to an additional aspect, an airway pressure breathing device includes an airway pressure breathing device body having at least one air passage to receive air and at least one passage to expel air, and a bi-directional exhalation valve. The bi-directional valve is coupled to the at least one air passage to receive air and the at least one air passage to expel air, and includes a valve body having a center chamber, a plurality of side chambers, and an elongated compartment and a plurality of bidirectional ports coupled to the center chamber via a set of passages to provide fluid ingress into the bi-directional valve in a first mode of operation or fluid egress from the bi-directional valve in a second mode of operation, and a plurality of unidirectional ports coupled to the plurality of bidirectional ports to provide providing fluid egress from the valve in the second mode of operation, and a single unidirectional port to provide fluid ingress into the bi-directional valve in the first mode of operation, and a mechanism including a center paddle and a plurality of side paddles, and a shaft supporting the center paddle and the plurality of side paddles along the length of the shaft, the shaft disposed in the elongated compartment of the valve body and allowed to pivot to cause the center paddle and the plurality of side paddles to open and close the input and output ports according the first and second modes.

The details of one or more embodiments of the invention are set forth in the accompanying drawings and the description below. Other features, objects, and advantages of the invention are apparent from the description and drawings, and from the claims.

DESCRIPTION OF DRAWINGS

FIGS. 3A-3I are somewhat isometric views of a bidirectional valve for the miniature CPAP device of FIGS. 1 and 2.

FIG. 4 is a diagram depicting the bidirectional valve in a mask of a more conventional CPAP.

DETAILED DESCRIPTION

Overview

As disclosed in the above co-pending incorporated by reference patent applications micro pumps can be made using micro fabrication methods and can be used for performing micro pumping processes that are widely implemented in industrial, medical, and biological applications. For example, micro pumps can be incorporated into CPAP devices. The micro pumps can transport fluids, e.g., gas or liquids, in small, accurately measured quantities. In some implementations, the micro pumps can transport the fluids at high flow rates, e.g., about microliters per second to about a few milliliters per second, and/or high pressure, e.g., about thousandths of one psi to about tenths of one psi. The micro pumps can be designed such that the fluid transport, the flow rates, and/or the pressure are scalable.

Figure 1:
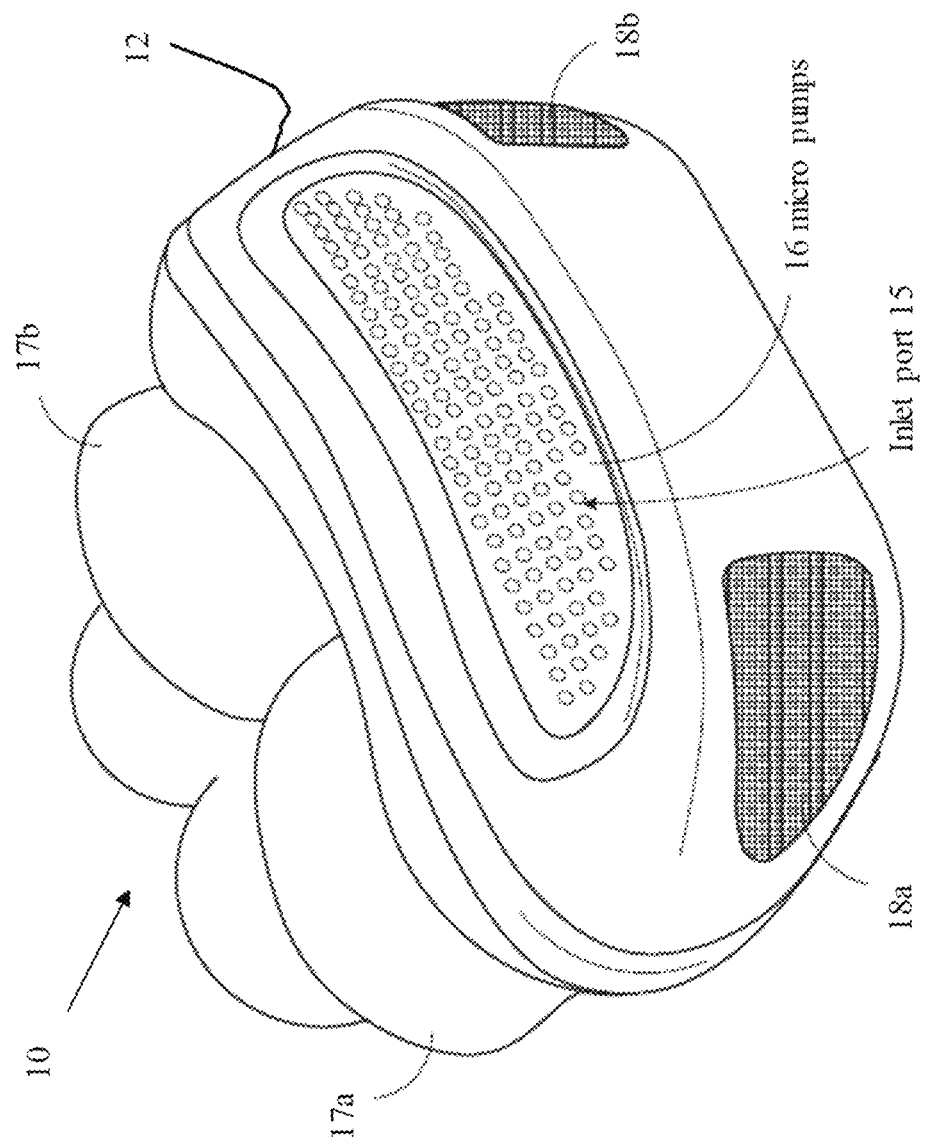
FIG. 1 is a diagram of a miniature CPAP device.

Referring now to FIG. 1, an autonomous device for treating breathing disorders 10 (device) is shown. The device 10 is a CPAP type (continuous positive airway pressure) breathing device. However, the CPAP device 10, unlike CPAP machines, is an autonomous device that is local to the nose and which provides a required amount of air flow at a required pressure to treat various breathing disorders such as obstructive sleep apnea ("OSA").

The CPAP device 10 can take a conceptual form as disclosed in the above applications. In this configuration, the CPAP device 10 includes a body 12 that houses micro pumps 16 here plural component-pump stacked elements generally denoted by a curved line, indicating that the micro pumps are disposed behind an inlet port 15. (See FIG. 2 for a functional location and the incorporated by reference applications for details.) The CPAP breathing device 10 includes a bi-directional valve that is used as an exhalation valve (not shown, but see FIGS. 2 and 3A-3H and 4). The CPAP device 10 has cushioned plugs 17a, 17b with air passages through the cushioned plugs 17a, 17b that provide a nasal interface. The cushioned plugs 17a, 17b are made of a generally rubbery material that makes a tight fit when inserted into a user's nostrils. The CPAP device 10 has one or as shown two outlets 18a, 18b for exhalation of air.

Figure 2:
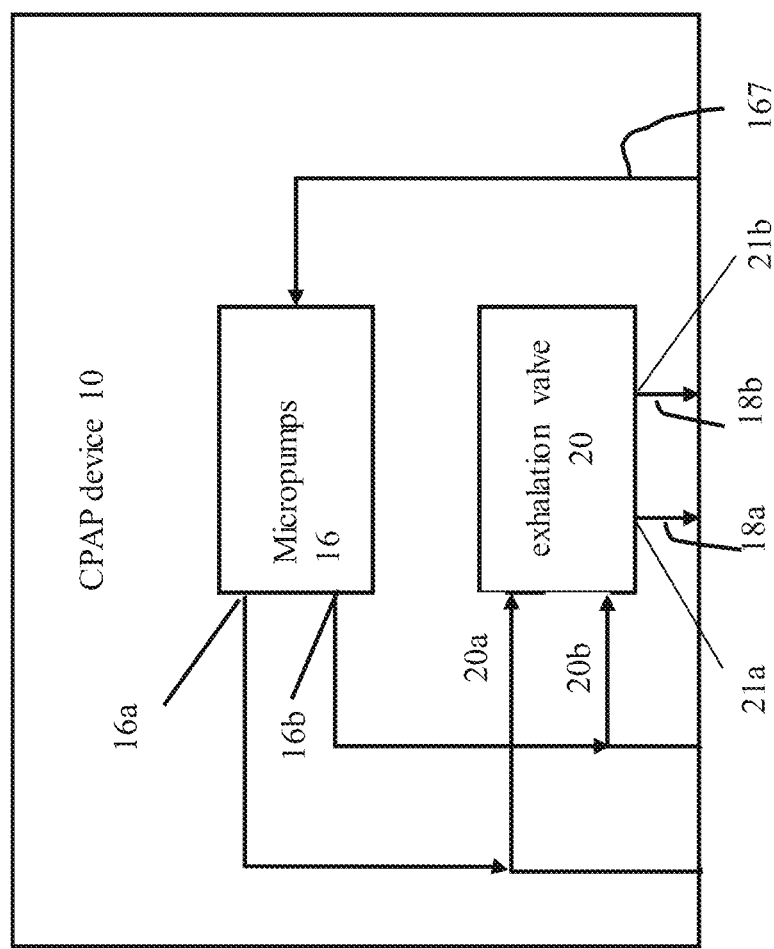
FIG. 2 is a functional block diagram of a miniature CPAP device employing micro pumps that operating in two opposite phases of a pumping cycle, as disclosed in the above published applications.

Referring now to FIG. 2, a schematic, e.g., of the configurations shown in FIG. 1, includes a bidirectional valve 20 coupled to the micro pump 16 within the CPAP device 10. As fluid, e.g., air is pushed into one or more inlet ports of the valve 20, the one or more inlets open and the valve 20 opens a passage from the one or more inlets to one or more bidirectional ports to expel the fluid, e.g., air from the bidirectional ports of the valve 20. When a fluid, e.g., air flow external to the valve is forced into the one or more bidirectional ports, the air flow pushes the inlet of the valve 20 shut while opening one or more outlet ports of the valve 20 at the end of the bidirectional ports. This action of the valve will occur even while air is blowing against the inlet ports provided the pressure exerted into the bidirectional ports is sufficient to overcome the pressure of air blowing against the inlet ports. In the context of a CPAP device the valve 20 is referred to herein as an exhalation valve 20.

The exhalation valve 20 has inlets 20a, 20b and outlets 21a, 21b. The exhalation valve 20 is coupled between the micro pumps 16 (via the exhalation valve inlets 20a, 20b and inlets 16a, 16b of the micro pump 16) and outlets 18a, 18b of the device 10, (via the exhalation valve ports 21a, 21b), as shown. The inlets 16a, 16b of the micro pump 16 are coupled to inlet port 15 of the CPAP device 10.

The above mentioned patent applications disclose an exhalation valve of a butterfly configuration having a flap that is disposed inside a passageway of the valve. The flap is rotatable about an axial member to open and close the passageway that is between a pair of ports and an outlet port. The exhalation valve 20 discussed below is an alternative to the exhalation valve in the above applications and will now be described.

Referring now to FIGS. 3A-3H, various views of the exhalation valve 20 having a bi-directional valve configuration is shown. The exhalation valve 20 has a paddle mechanism that uses air flow from the micro pumps 16 to close passages in the exhalation valve 20 at the end of an exhalation/beginning of pause in breathing and at the beginning of exhalation. The exhalation valve 20 opens even as the micro pumps blow air on the exhalation valve 20. The CPAP device 10 is configured to select how much of the micro pumps' 16 air flow is needed to push the valve 20 shut. Pressure from the micro pumps 16 will hold the exhalation valve 20 shut prior to exhalation. All of the exhalation air flow from a user is applied to the exhalation valve 20 to open the exhalation valve 20. The shape of the valves' flaps on the paddle may be optimized to assist the exhalation valve 20 to remain open during exhalation. In addition, weak magnetics may also be used to keep exhalation valve 20 open or closed depending on details of a design. The exhalation air from a user would generally be sufficient to overcome a minimum amount of air flow from the micro pump to keep the exhalation valves 20 closed.

Referring now to FIG. 3A, show is the valve 20 including a body 41, a single unidirectional port 43 that is in this implementation used as an inlet, bi-directional ports 45a and 45b, a plurality of unidirectional ports that are in this implementation used as outlet ports 47a, 47b. Each of the outlet ports 47a, 47b has a side paddle (or flap) 49a, 49b, respectively that selectively closes and opens the respective port 47a, 47b. The inlet port 43 also has a central paddle (or flap) 51. The side paddles 49a, 49b and 51 are flat members and are part of paddle valve mechanism 55. The paddle valve mechanism 55 is rotatable with an axial compartment 57 (FIG. 3B) provided in the body 41 at body portion 41a to open and close passageways among ports 43, 45a, 45b, and 47a, 47b, as will be described.

FIG. 3B shows the arrangement of FIG. 3A in an exploded view. This view shows passages 46a, 46b and 50 through the body 41. As shown in FIG. 3B the body 41 has the bi-directional ports 45a and 45b and outlet ports 47a, 47b coupled by cylindrical members or portions 41b, 41c of the body 41, the single unidirectional port 43 provided by a rectangular member or portion 41c of the body 41, and the axial compartment 57 that receives the paddle valve mechanism 55.

FIG. 3C shows the paddle valve mechanism 55 with the side paddles 49a, 49b, at the ends of the shaft 53 and the central paddle 51 disposed (centrally) between the side paddles 49a, 49b. The side paddles 49a, 49b are orthogonal to the central paddle 51 and are supported on the shaft 53 that rotationally pivots about its axis when disposed in the axial compartment 57 (FIG. 3B). The mechanism 55 also includes an compartment seal 65.

While, the central paddle 51 in this embodiment is generally orthogonal to the side paddles 49a, 49b other configurations of the body 41 could provide other positioning configurations of the side paddles 49a, 49b on the shaft 53. Also while two side paddles 49a, 49b (and hence two bidirectional ports 45a, 45b and two outlet ports 47a, 47b are shown) more or fewer side paddles may be used. Also while a single inlet port 43 is shown in some configurations plural inlet ports could be used. Configurations with more than two outlet ports and two bi-directional ports and more than one inlet port would necessitate adjustments to the mechanism 55.

Referring now to FIGS. 3D-3E, these views show the valve 20 from a front elevation view (FIG. 3D) and frontal view broken away (FIG. 3E) exposing internal passages 63a, 63b and chambers 60a, 60b and 61. The chambers 60a, 60b are side chambers and are shown disposed between outlet ports 47a, 47b and bidirectional ports 45a, 45b. The chamber 61 is a central chamber. The passages 63a, 63b are provided from central chamber 61 to the side chambers 63a, 63b, as also shown. Also shown in FIGS. 3D-3E is an axial compartment seal 65 that seals the axial compartment 57 of FIG. 3A. In FIG. 3D the cross sections "FIG. 3G" and "FIG. 3I" reference FIGS. 3G and 3I, respectively.

Referring now to FIGS. 3F-3G, these views (somewhat simplified in cutaway view) show the valve 20 in a first mode of operation. FIGS. 3F-3G show internal details of the central chamber 61 and the passageways 63*a*, 63*b* (63*b* being shown in FIGS. 3F-3G) in which the paddle valve mechanism 55 rotates within the axial compartment 57 provided by the body 41 to force the central paddle 51 into the open position. When central paddle 51 is in the open position (upright as shown in FIG. 3G) that opens the one way inlet port 43 and allows air to flow through orifice or passage (only 63*b* is labeled) between center chamber 61 and side chambers 60*a*, 60*b* (only 60*b* is labeled), while forcing the side paddles 49*a*, 49*b* to close the air outlet ports 47*a*, 47*b*. This mode allows air to flow from the inlet port 46 to the bidirectional ports 45*a*, 45*b*, but not out the air outlet ports 47*a*, 47*b*, as denoted by the arrows labeled 70 (shown for one side of the valve 20). This would correspond to the user inhaling air from the micro pumps 16.

FIGS. 3H-3I show internal details of the central chamber 61 and the passageways 63 in which the paddle valve mechanism 55 rotates within the axial compartment 57 provided by the body 41 to force the central paddle 51 into the closed position that closes the one way inlet port 43 and inhibits air to flow through orifice or passage (only 63*b* is labeled) between center chamber 61 and side chambers 60*a*, 60*b*, while forcing the side paddles 49*a*, 49*b* to open the air outlet ports 47*a*, 47*b*. This mode allows air to flow from the bidirectional ports 45*a*, 45*b* out the air outlet ports 47*a*, 47*b*, as denoted by the arrows labeled 72 (shown for one side of the valve 20). This would correspond to the user exhaling air from the user's nostrils.

Passages between the air outlet ports 47*a*, 47*b* and the bidirectional ports 45*a*, 45*b* are, in general rounded, but other shapes could be used. Passages 63*a*, 63*b* can be rounded, oblong, etc. The central passage 61 is somewhat rectangular. However, any shapes could be used for the passages, ports, chambers, etc. and in general all surfaces and interior passages, ports, chambers, etc. are smooth. Dimensions of the various components of the exhalation valve 20 would be selected according to various design considerations, such as the volume of air that will be convected during modes of operation, the size of the CPAP device 10, and available space within the CPAP device 10.

Thus the bi-directional exhalation valve 20 includes the valve body 41 having the center chamber 61 and a plurality of side chambers (here two) 60*a*, 60*b*, and the elongated compartment 57. The plurality of bidirectional ports 45*a*, 45*b* (here two) are coupled to the center chamber 61 via the set of passages 63*a*, 63*b* to provide fluid ingress into the bi-directional valve 20 in a first mode of operation (inhalation) or fluid egress from the bi-directional valve 20 in a second mode of operation (exhalation). The output ports 47*a*, 47*b* are coupled to the plurality of bidirectional ports to provide fluid egress from the valve in the exhalation mode of operation, and a single unidirectional port 51 to provide fluid ingress into the bi-directional valve 22 inhalation. The paddle mechanism including the center paddle and the plurality of side paddles, and a shaft supporting the center paddle 51 and the plurality of side paddles 49*a*, 49*b* along the length of the shaft 53, the shaft 53 is arranged in the elongated compartment of the valve body, such that the shaft 53 is rotatable within the elongated compartment in the body.

The bi-directional valve 20 when used as the exhalation valve 20 in the CPAP device may allow a user to more easily overcome pressure caused by incoming air from the micro pump (micro blowers) during exhalation of air from the nose passages. This provides a more comfortable and improved breathing experience with CPAP device 10. When used in an airway pressure breathing device, e.g., the CPAP device 10, the bi-directional exhalation valve 20 is coupled to the at least one air passage to receive air from the CPAP device (e.g., the micro pump in a micro CPAP device or from a conventional CPAP) and the at least one air passage to expel air. The CPAP airway pressure breathing device 10 body has at least one air passage to receive air from a source of air, and which is coupled to the plurality of bidirectional ports of the bi-directional exhalation valve 20. The CPAP device 10 also has at least one passage to expel air that is coupled to the plurality of unidirectional ports of the bi-directional exhalation valve 20. The airway pressure breathing device can have the source of air being a micro pump supported by the airway pressure breathing device body where the micro pump is configured to pump ambient air through the air passages and the bi-directional exhalation valve.

Not being bound by the foregoing, but in the context of a CPAP device, operation can be approximated as follows: during inhalation, pressure $P_b$ at the bidirectional ports is approximately related to $P_b = P_i + P_h$ (the sum of pressure from the micro pump $P_i$ plus the pressure of inhalation $P_h$), whereas during exhalation pressure $P_b$ at the bidirectional ports is approximately related to $P_b = P_e + P_i$ (the sum of pressure from exhalation $P_e$ (a negative pressure or vacuum) plus the pressure $P_i$ from the micro pump, a positive pressure). Provided that $P_b$ is positive during inhalation and $P_b$ is negative during exhalation, the valve 20 will operate in a bidirectional manner.

In other embodiments, the airway pressure breathing device body is a mask that is configured to be secured over a user's head and/or against a user's nostrils, with the mask configured to receive a hose as discussed below in FIG. 4.

Referring now to FIG. 4, a mask 80 is shown, which mask 80 is typical of a conventional nasal mask used with conventional CPAP machines (not shown). The mask 80 includes a hose attachment 82 (for a hose 84 that couples to the CPAP machine) and has a harness 86 that secures the mask 80 to the user positioning air outlets under the nose of a user. Unlike a conventional mask, the mask 80 also includes the exhalation valve 20 that is fitted to and positioned within the mask 80 such that the exhalation valve 20 allows a user to more easily overcome pressure caused by incoming air from the CPAP machine during exhalation of air from the nose passages, by use of the operations depicted in FIGS. 3E-3H. Thus, the exhalation valve 20 would be connected in the mask 80 in such a manner that an outlet (not referenced) from the hose 84 is coupled to the inlet port 51 of the exhalation valve 20. The outlet ports 47*a*, 47*b* of the exhalation valve 20 would be coupled to corresponding ports on the mask 80, which are used to expel air during exhalation. The bidirectional ports 45*a*, 45*b* are coupled to plugs (not shown) having openings to allow the user to breath air in (via the inlet port 51) and expel air out (via the outlet ports 47*a*, 47*b*).

In order to satisfy various design considerations for different types of masks as well as different configurations of CPAP devices 10 the physical form of the exhalation valve may be altered from that shown in the figures.

Various techniques can be used to produce the exhalation valve 20, including molding the device from suitable (medical grade) plastic materials, 3D printing techniques, and so forth.

The exhalation valve 20 would generally have dimensions suitable for the application. Thus for example in the CPAP device 10 as envisioned in the incorporated by reference applications the dimensions are on the order of 10's or 100's of millimeters. In some applications of the exhalation valve 20 the valve can be smaller or larger.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein. Other embodiments are within the scope of the following claims.

What is claimed is:

1. A bi-directional valve comprises:
    a valve body having a center chamber, a plurality of side chambers, and an elongated compartment and a plurality of bidirectional ports coupled to the center chamber via a set of passages to provide fluid ingress into the bi-directional valve in a first mode of operation or fluid egress from the bi-directional valve in a second mode of operation, and a plurality of unidirectional ports that are output ports coupled to the plurality of bidirectional ports to provide fluid egress from the valve in the second mode of operation, and a single unidirectional port that is an input port to provide fluid ingress into the bi-directional valve in the first mode of operation; and
    a mechanism comprising a center paddle and a plurality of side paddles, and a shaft supporting the center paddle and the plurality of side paddles along the length of the shaft, the shaft disposed in the elongated compartment of the valve body and allowed to pivot to cause the center paddle and the plurality of side paddles to open and close the single unidirectional port and the plurality of unidirectional ports according the first and second modes.

2. The valve of claim 1 wherein the plurality of unidirectional ports are coupled to the bidirectional ports by a pair of portions of the body.

3. The valve of claim 1 wherein the input port is orthogonal to the outlet ports.

4. The valve of claim 1 wherein the mechanism opens the single unidirectional port and closes the unidirectional ports in the first mode of operation.

5. The valve of claim 1 wherein the mechanism closes the single unidirectional port and opens the unidirectional ports in the second mode of operation.

6. The valve of claim 1 wherein the mechanism opens the single unidirectional port and closes unidirectional ports in the first mode of operation and allows fluid from the single unidirectional port to egress from the bidirectional ports.

7. The valve of claim 1 wherein the mechanism closes the single unidirectional port and opens the unidirectional ports in the second mode of operation and allows fluid from the bidirectional ports to egress from the unidirectional ports.

8. The valve of claim 1 wherein the center paddle is orthogonal to the plurality of side paddles on the shaft.

9. The valve of claim 1 further comprising:
    a shaft seal member to hold the shaft in the elongated compartment in the valve body.

10. An airway pressure breathing device comprises:
    an airway pressure breathing device body having at least one air passage to receive air and at least one passage to expel air; and
    a bi-directional exhalation valve, the bi-directional valve coupled to the at least one air passage to receive air and the at least one air passage to expel air, the bi-directional exhalation valve comprising:
        a valve body having a center chamber, a plurality of side chambers, and an elongated compartment and a plurality of bidirectional ports coupled to the center chamber via a set of passages to provide fluid ingress into the bi-directional valve in a first mode of operation or fluid egress from the bi-directional valve in a second mode of operation, and a plurality of unidirectional ports that are output ports coupled to the plurality of bidirectional ports providing fluid egress from the valve in the second mode of operation, and a single unidirectional port that is an input port to provide fluid ingress into the bi-directional valve in the first mode of operation; and
        a mechanism comprising a center paddle and a plurality of side paddles, and a shaft supporting the center paddle and the plurality of side paddles along the length of the shaft, the shaft disposed in the elongated compartment of the valve body and allowed to pivot to cause the center paddle and the plurality of side paddles to open and close the input and output ports according the first and second modes.

11. The airway pressure breathing device of claim 10 wherein the airway pressure breathing device body has the at least one air passage to receive air coupled to a source of air and the plurality of bidirectional ports of the bi-directional exhalation valve, and the at least one passage to expel air coupled to the plurality of unidirectional ports of the bi-directional exhalation valve.

12. The airway pressure breathing device of claim 11 wherein the source of air is a micro pump supported by the airway pressure breathing device body.

13. The airway pressure breathing device of claim 10 further comprising:
    a micro pump supported by the airway pressure breathing device body, the micro pump configured to pump ambient air through the set of passages and the bi-directional exhalation valve.

14. The airway pressure breathing device of claim 10 wherein the airway pressure breathing device body is a mask that is configured to be secured over a user's head or against a user's nostrils.

15. The airway pressure breathing device of claim 14 wherein the bi-directional exhalation valve is supported in the mask.

16. The airway pressure breathing device of claim 14 wherein the mask is configured to receive a hose.

* * * * *